United States Patent
Vasyukevich et al.

(10) Patent No.: US 9,814,774 B2
(45) Date of Patent: Nov. 14, 2017

(54) DERMATOLOGICAL PRODUCT

(71) Applicant: NYCFS, LLC, New York, NY (US)

(72) Inventors: Konstantin Vasyukevich, New York, NY (US); Dilip D. Madnani, New York, NY (US)

(73) Assignee: NYCFS, LLC, New York, NY (US)

( * ) Notice: Subject to any disclaimer, the term of this patent is extended or adjusted under 35 U.S.C. 154(b) by 26 days.

(21) Appl. No.: 14/456,464

(22) Filed: Aug. 11, 2014

(65) Prior Publication Data
US 2015/0079011 A1    Mar. 19, 2015

Related U.S. Application Data

(60) Provisional application No. 61/864,887, filed on Aug. 12, 2013.

(51) Int. Cl.

| | | |
|---|---|---|
| *A61K 36/72* | (2006.01) | |
| *A61K 47/34* | (2017.01) | |
| *A61K 8/25* | (2006.01) | |
| *A61K 45/06* | (2006.01) | |
| *A61K 47/24* | (2006.01) | |
| *A61K 8/58* | (2006.01) | |
| *A61Q 19/00* | (2006.01) | |
| *A61K 8/891* | (2006.01) | |
| *A61K 8/92* | (2006.01) | |
| *A61K 36/752* | (2006.01) | |
| *A61K 36/185* | (2006.01) | |
| *A61K 36/28* | (2006.01) | |
| *A61K 36/61* | (2006.01) | |
| *A61K 36/738* | (2006.01) | |
| *A61Q 17/04* | (2006.01) | |
| *A61Q 19/08* | (2006.01) | |

(52) U.S. Cl.
CPC .............. *A61K 45/06* (2013.01); *A61K 8/585* (2013.01); *A61K 8/891* (2013.01); *A61K 8/922* (2013.01); *A61K 36/185* (2013.01); *A61K 36/28* (2013.01); *A61K 36/61* (2013.01); *A61K 36/738* (2013.01); *A61K 36/752* (2013.01); *A61K 47/24* (2013.01); *A61Q 19/00* (2013.01); *A61Q 17/04* (2013.01); *A61Q 19/08* (2013.01)

(58) Field of Classification Search
None
See application file for complete search history.

(56) References Cited

U.S. PATENT DOCUMENTS

| | | | |
|---|---|---|---|
| 6,221,918 B1 * | 4/2001 | Siderov | A23L 1/3002 514/762 |
| 2005/0152993 A1 * | 7/2005 | De Oliveira | A61K 36/185 424/669 |
| 2009/0246156 A1 * | 10/2009 | Kunin | A61K 8/35 424/60 |
| 2010/0196454 A1 * | 8/2010 | Keller | A61K 8/585 424/450 |

\* cited by examiner

*Primary Examiner* — Abigail Fisher
(74) *Attorney, Agent, or Firm* — Gottlieb, Rackman & Reisman, P.C.

(57) ABSTRACT

An improved composition for alleviating and treating the condition of scarring is provided. The system is directed to a product or composition which includes a silicone compound as a delivery medium, to which an oil compound such as sea buckthorn oil as an antioxidant is added. The product is prepared by mixing the two ingredients.

13 Claims, No Drawings

DERMATOLOGICAL PRODUCT

RELATED APPLICATION(S)

This application is based on and claims priority to U.S. Provisional Patent Application No. 61/864,887 filed on Aug. 12, 2013.

FIELD OF THE INVENTION

This invention is directed to a dermatological product, specifically a composition for dermatological application to minimize scarring.

BACKGROUND OF THE INVENTION

Surgical scars may be unsightly and are generally unwanted; this is especially the case after cosmetic procedures. Certain techniques for minimizing scars are known and include: cleaning the affected area; bandaging the affected area; and avoiding unnecessary contact with the affected area. Additionally, there are a number of products marketed towards scar prevention. Examples of these products include: bio-oils such as calendula, lavender, rosemary, cherobe vitamins; dermatix ultra (a topical silicone/unique silicone combination); scar away silicone sheets; kelocote (a silicone product); mederma (water, Aloe, onion extract); revitol (herbal remedy); scar esthetique (silicone, arnica, antioxidants, lipopeptides, coQ10, dimethicone, calendula, onion extract, vitamins c, d, and e, seaweed extract); Scarpin (silicone gel); taslyn-CI (lipid peptides, fatty acids, botanical extracts); bio skin repair (oils, squalen, hyaluronic acid); newbiotic (natural oils, including seabuckthorn in a 'secret formula').

None of the products has combined only silicone and sea buckthorn (seaberry) oil in the presently disclosed formulation. Further, none has demonstrated the unexpected and beneficial effects of the presently disclosed formulation.

Accordingly, it would be desirable to provide an improved composition for ameliorating scarring.

SUMMARY OF THE INVENTION

Generally speaking, in accordance with the invention, an improved composition for alleviating and treating the condition of scarring is provided. The system is directed to a product or composition which includes a silicone compound as a delivery medium, to which an oil compound such as sea buckthorn oil is added. The product is prepared by mixing the two ingredients.

Additional ingredients may be added to the inventive composition, including a sunscreen compound, a medicinal compound and a burn treatment compound.

Accordingly, it is an object of the invention to provide an improved dermatological product.

Another object of the invention is to provide a dermatological product for minimizing scarring.

A further object of the invention is to provide a dermatological product which also exhibits sun-blocking properties, anti-inflammatory properties and bruise treatment properties.

Yet another object of the invention is to provide a dermatological product which is easy to apply.

Still other objects and advantages will be apparent from the following description.

DETAILED DESCRIPTION OF THE INVENTION

The inventive dermatological product includes one or more silicone compounds as the delivery medium. The one or more silicone compounds may be present in an amount between about 40.0 and 99.9 weight percent of the overall composition. Preferably, the silicone compounds are present in an amount between about 80 and 99 weight percent. The preferred silicone compounds are selected from cyclopentasiloxane, cyclotetrasiloxane and dimethicone. Other silicone compounds that are suitable include cyclomethicone, dimethicone copolyol, polysiloxane, silicone dioxide and polydimethylsiloxane.

The inventive product also includes an oil. The oil may be present in an in an amount between about 0.01 and 50 weight percent, with between about 0.1 and 5 weight percent being preferred. The preferred oil is sea buckthorn oil, although other medical oils such helichrysum oil, tea tree oil, neroli oil and rosehip seed oil can be used. Sea buckthorn oil is an oil that is extracted from the seeds, fruit and/or leaves of the plant species *Hippophae Rhamnoides*, which is found mainly in Eastern Europe and Central Asia, Sea buckthorn oil is known to have significant anti-oxidant, anti-inflammatory effects. It is obtained from the company Liberty Natural, Inc. located in 20949 S Harris Rd, Oregon City, Oreg. 97045. Sea buckthorn oil contains essential fatty acids, vitamins and other nutrients which are ideal for skin nutrition and scar improvement. The purpose of the oil in the inventive product is to enhance healing. In preparing the inventive composition, the oil is mixed with the silicone compound until the composition is uniform.

The inventive product may also include a sunscreen compound. The sun screen compound may be present in the overall composition in an amount no greater than about 50% weight percent and should be present in an amount between about 5% and 25% weight percent. The sun screen compound is added to the inventive composition in order to provide sun-blocking properties. Suitable sun screen compounds include titanium dioxide, zinc oxide, octyl salicylate, avobenzone, homosalate, octylcrylene, oxybenzene and octyl methoxycinnamate. This ingredient is added to the inventive composition by mixing together until the composition is uniform.

Optionally, the inventive product includes an anti-inflammatory compound. The anti-inflammatory compound may be present in the overall composition in an amount no greater than 5% weight percent and should be in an amount between about) 0.1% and 5% weight percent. The preferred anti-inflammatory compound is hydrocortisone. The anti-inflammatory compound is added to the inventive composition by mixing until uniform composition.

Optionally, the inventive product includes an antibiotic compound. The antibiotic compound should be added to the composition in either powder or solution found by determining its strength, as well known in the medical art, and as authorized under FDA guidelines. The preferred antibiotic compound is bacitracin (USP 400 U in 1 gm—preferred) or neomycin (USP 3.5 mg in 1 gm—preferred). Other suitable antibiotic compounds include polymyxin B (USP 5,000 U in 1 gm—preferred). The antibiotic compound is added to the inventive composition by mixing until the composition is uniform.

Optionally, the inventive product includes a bruise treatment compound. The bruise treatment compound may be present in the overall composition in an amount up to 50% weight percent, and is preferably present in the overall composition in an amount between about 5% and 25% weight percent. The preferred bruise treatment compound is *arnica montana* which is homeopathic oil made from the *arnica montana* plant. Others include chamomile, lavender, St. John's Wort, calendula and preparations made from the *Spongilla lacustris* sponge species. The bruise treatment compound is added to the inventive composition by mixing together until the composition is uniform.

A preferred formulation of the inventive product is as follows:

| Chemical Name | Weight Percentage |
| --- | --- |
| sea buckthorn oil | 0.1-5% |
| cyclopentasiloxane | 40-60% |
| cyclotetrasiloxane | 30-50% |
| dimethiconol | 10-30% |

The dermatological product of the invention is generally applied to a patient's skin in a sufficient quantity to cover the affected area. In a preferred embodiment, the dermatological product is a liquid gel product, although it may also be provided in a spray form.

A clinical test of thirty (30) patients receiving the dermatological product to treat scarring was performed. All thirty patients self-reported that the appearance of their scar improved after a completed course of topically applying the dermatological product to existing scars; and all thirty patients reported that they were satisfied with the results. Additionally, twenty-nine (96%) of the patients said they would recommend the product to a friend and only one patient (3.4%) reported minor side effects.

Patients involved in the test were also asked to rate the improvement of the appearance of their scars as a result of the treatment. Patients were asked to rate the improvement as one of: 0%; 25%; 50%; 75%; or 100%. Seventeen patients were treating surgical incisions and the average of these patients improvement ratings was 54%. Fourteen patients were treating keloid/old scars and the average of these patients' improvement ratings was 46%. Five patients were treating pigmented scars/burns and the average of these patients' improvement ratings was 75%.

The test data demonstrate that treatment in accordance with the invention significantly reduces the effects of scarring.

This disclosure only illustrates several embodiments of a dermatological product, however, other types and variations are possible, and the disclosure is not intended to be limiting in that regard. Thus, although the description above contains much specificity, the details provided should not be construed as limiting the scope of the embodiments but merely as providing illustrations of some of the presently preferred embodiments. The description is not to be taken as restrictive on the scope of the embodiments and is understood as a broad and general teaching in accordance with the present invention. While the present embodiments of the invention have been described using specific terms, such description is for present illustrative purposes only, and it is to be understood that modifications and variations to such embodiments, including but not limited to the substitutions of equivalent features, compounds, or substances, and the reversal of various features thereof, may be practiced by those of ordinary skill in the art without departing from the spirit and scope of the invention.

The scope of the invention will now be defined in the following claims.

The invention claimed is:

1. A method of treating scarring comprising the step of topically administering to a patient an effective amount of a uniformly mixed dermatological composition comprising a silicone compound selected from the group consisting of cyclopentasiloxane, cyclotetrasiloxane and dimethicone, and sea buckthorn oil
    wherein the silicone compound is present in the overall composition in an amount between about 40.00 and 99.9 weight percent and the sea buckthorn oil is present in the overall composition in an amount between about 0.01 and 50 weight percent.

2. The method of claim 1, wherein the composition further includes a sunscreen compound selected from the group consisting of octyl salicylate, avobenzone, homosalate, octylcrylene, oxybenzene and octyl methoxycinnamate, titanium dioxide and zinc oxide.

3. The method of claim 1, wherein the composition further includes at least one of cortisone as an anti-inflammatory, bacitracin or neosporin or polymyxin b as an antibiotic, and *arnica montana* as a bruise treatment compound.

4. A method of treating scarring comprising the step of topically administering to a patient an effective amount of a uniformly mixed dermatological composition comprising a silicone compound present in the overall composition in an amount between about 80 and 99 weight percent and an oil compound present in the overall composition in an amount between about 0.1 and 5 weight percent,
    wherein the silicone compound is selected from the group consisting of cyclopentasiloxane, cyclotetrasiloxane, dimethicone, cyclomethicone, dimethicone copolyol, polysiloxane, silicone dioxide and polydimethylsiloxane, and the oil compound is sea buckthorn oil.

5. The method of claim 4, wherein the composition further includes a sunscreen compound in an amount no greater than about 50% weight percent.

6. The method of claim 4, wherein the composition further includes at least one of an anti-inflammatory compound, an antibiotic and a bruise treatment compound.

7. A method for treating scarring comprising the step of topically administering to a patient an effective amount of a uniformly mixed composition comprising a silicone compound and an oil compound
    wherein the silicone compound is present in the overall composition in an amount between about 40.0 and 99.9 weight percent,
    wherein the oil compound is present in the overall composition in an amount between about 0.01 and 50 weight percent, and
    wherein the oil compound is sea buckthorn oil.

8. The method of claim 7, wherein said composition further includes one or more ingredients selected from the group consisting of a sun screen compound and a medicinal compound.

9. The method of claim 8, wherein the medicinal compound is at least one of an anti-inflammatory, an antibiotic and a bruise treatment compound.

10. The method of claim 7, wherein the composition further includes a sun screen compound.

11. The method of claim 10, wherein the sun screen compound is selected from the group consisting of titanium dioxide, zinc oxide, octyl salicylate, avobenzone, homosalate, octylcrylene, oxybenzene and octyl methoxycinnamate.

12. The method of claim 7, wherein the composition further includes a medicinal compound selected from the group consisting of an anti-inflammatory, an antibiotic and a bruise treatment compound.

13. The method of claim 12, wherein the anti-inflammatory is cortisone and the antibiotic is at least one of bacitracin, neomycin and polymyxin b.

* * * * *